(12) United States Patent
Gaetani et al.

(10) Patent No.: US 8,349,317 B2
(45) Date of Patent: Jan. 8, 2013

(54) USE OF L-CARNITINE OR AN ALKANOYL L-CARNITINE, FOR THE PREPARATION OF A DIETARY SUPPLEMENT OR MEDICAMENT FOR THE TREATMENT OF CORNEAL DISEASE

(75) Inventors: Franco Gaetani, Ariccia (IT); Janos Feher, Montopoli in Sabina (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 1127 days.

(21) Appl. No.: 11/993,559

(22) PCT Filed: Jun. 30, 2006

(86) PCT No.: PCT/EP2006/063769
§ 371 (c)(1),
(2), (4) Date: May 13, 2008

(87) PCT Pub. No.: WO2007/006672
PCT Pub. Date: Jan. 18, 2007

(65) Prior Publication Data
US 2010/0034795 A1    Feb. 11, 2010

(30) Foreign Application Priority Data
Jul. 8, 2005    (EP) .................................... 05014812

(51) Int. Cl.
*A61K 38/43*    (2006.01)
*A61K 31/20*    (2006.01)
*A01N 37/00*    (2006.01)
(52) U.S. Cl. ........................................ 424/94.1; 514/558
(58) Field of Classification Search .................. 424/94.1; 514/558
See application file for complete search history.

(56) References Cited

U.S. PATENT DOCUMENTS

| 5,753,703 A | * | 5/1998 | Cavazza et al. | ............... 514/556 |
| 6,335,038 B1 | * | 1/2002 | Cavazza | ........................ 424/757 |
| 2005/0074443 A1 | | 4/2005 | Treadwell | |

FOREIGN PATENT DOCUMENTS

| CA | 2 291 959 | 6/2001 |
| WO | WO 01/37851 | 5/2001 |
| WO | WO 2004/004599 | 1/2004 |
| WO | WO 2004/006801 | 1/2004 |
| WO | WO 2005/063223 | 7/2005 |

OTHER PUBLICATIONS

Gould, Philip, Salt selection for basic drugs, 1986, Int. J. of Pharm., 33, pp. 201-217 (18 pages in all).*
Dry Eye Center of Maryland, Last Accessed Jul. 13, 2011, 2 pages, http://www.dryeyecenterofmd.com/.*
Xenophilia, Dry Eye Syndrome, Xenophilia, Last accessed Oct. 31, 2011, pp. 1-21, http://web.archive.org/web/20041014002846/http://www.xenophilia.com/zb0061.htm.*
Fox et al, Sjogren's Syndrome: A Guide for the Patient, 2002, http://dry.org/fox20020816/guide.htm, last accessed Jan. 27, 2012, pp. 1-45.*
R. Brancato, et a., Prevention of Cornealkeratocyte Apoptosis After . . . , European Journal of Ophthalmology, vol. 10, No. 1, pp. 32-38, 2000.
Nicholas A. Phelps Brown, et al., Nutrition Sipplements and The Eye, Eye, vol. 12, pp. 127-133, 1998.
Giiuffride S, et al., Essential Fatty Acids . . . , vol. 41, No. 4, pp. S275, 2000.

* cited by examiner

Primary Examiner — Daniel Sullivan
Assistant Examiner — Trevor Love
(74) Attorney, Agent, or Firm — Lucas & Mercanti, LLP

(57) ABSTRACT

Use of L-carnitine and/or one or more alkanoyl L-carnitines or one of their pharmaceutically acceptable salts for the preparation of a dietary supplement or medicament for the treatment of corneal diseases is disclosed.

13 Claims, No Drawings

USE OF L-CARNITINE OR AN ALKANOYL L-CARNITINE, FOR THE PREPARATION OF A DIETARY SUPPLEMENT OR MEDICAMENT FOR THE TREATMENT OF CORNEAL DISEASE

The present invention relates to the use of L-carnitine and/or one or more alkanoyl L-carnitines in combination with a lipid-soluble benzoquinone and a polyunsaturated fatty acids, for the preparation of dietetic supplements and medicaments useful for the prevention and treatment of diseases of the cornea.

The corneal epithelium is the outermost layer of the cornea, many diseases can damage this delicate structure and cause de-epithelialisation. The main causes of impairment of the epithelial structure of the cornea are dry eye syndrome, corneal abrasions and injuries, the mechanical action due to the application of contact lenses and refractive laser surgery.

Other diseases of the cornea are associated with impairment of the normal transparency of the corneal surface, caused, for example, by damage in the aftermath of keratitis, particularly bacterial, viral or fungal keratitis; by damage resulting from trauma and refractive laser surgery; as well as degenerative or hereditary diseases such as chronic and acute keratocono.

The tear film, which coats the corneal epithelium and is essential for the homeostasis of the eye surface, performs an important optical function, acting as a lubricant between the eyelids and the eyeball and as a vehicle for oxygen, guaranteeing the metabolism of the cells of the corneal epithelium; it also performs a flushing function, ensuring the removal of external agents. Also important, is its function as a carrier for growth factors, neuropeptides, and neuromodulators that regulate the activation, proliferation and differentiation of corneal and conjunctival epithelial cells. It also transports immunoglobulins (IgA, IgG, IgE), complement factors (C3, C4, C5), metalloproteases (MMP-2, 4, 9), enzymes (lysozyme, lactoferrin) and immune system cells, thus performing a fundamental defensive function against infections.

As mentioned above, there are diseases in which this homeostasis is impaired.

Dry eye syndrome is characterised by a quantitative (hypolacrimation) and/or qualitative (dyslacrimation) impairment of the tear film of multifactorial origin which may or may not cause clinically significant damage to the eye surface. The prevalence of dry eye syndrome ranges from 10 to 40% in the adult population and there is a highly significant correlation with age.

In the United States the prevalence of mild-to-moderate dry eye syndrome is up to approximately 10 million people (*Am. J. Ophthalmol:,* 1997; 124:723-728; *Arch Ophthalmol,* 2000; 118: 1264-1268).

Various studies conducted in order to understand the mechanisms activated in this disease have shown that the tears of subjects affected by dry eye syndrome present: an increased evaporation rate, increased surface tension, reduced vitamin A concentration, increased osmolality, reduced concentration of a number of proteins (lysozyme, lactoferrin), insufficient mucus production or qualitative changes in mucus production, with consequent, inadequate reconstruction of the mucus layer, reductions in a number of growth factors (EGF, TGF-α, aFGF-bFGF, LG-F, HGF) (*Contactologia,* 1982; 4: 34-37), changes in concentration of inorganic elements, reduced androgens and dysregulation of T lymphocyte activity (*Cornea,* 2005; 24: 1-7).

The clinical signs regarded as being most closely related to this pathological condition are reduced break-up time (BUT test) and Schirmer test results as are described in all textbooks for graduate students. (*Pescosolido N.: Le alterazioni del film lacrimale. In Stendler P.: "il sistema lacrimale", Fabiano editors, Canelli (AT),* 2000; pag. 237-330; hereinafter this reference will be referred to as *Pescosolido* 2000).

The BUT test has to do with the mucin content of the tear film and, in the dry eye, yields only values below 5 seconds. The Schirmer test, on the other hand, has to do with the water content of the tear film and, in the dry eye, yields values below 5 millimetres in 5 minutes.

The patient presents the following symptoms: foreign body sensation, burning, difficulty blinking, bruit on opening the eyelids, itching, eye fatigue, photophobia, blurred vision, and mucus extravasation at the inner canthi.

The treatment of this syndrome is based on the use of the following:
 (1) tear substitutes whose task is the regular moisturising of the cornea, but which do not exert any action on the basic causes of the disease and are endowed only with very short-lasting efficacy;
 (2) inserts (plugs) in the lacrimal canaliculus;
 (3) immunoregulators such as topical cyclosporin; topical steroids; anti-inflammatory agents (rumexilone and loteprednol); autologous serum (cytokine inhibitors);
 (4) topical or systemic androgens;
 (5) mucus (HETE eicosanoid) and aqueous (P2Y2 agonists) secretogenic substances;
 (6) acquaporins and agents such as antibiotics and detergents for the treatment of blepharitis (*Cornea,* 2005; 24; 1-7),
 Also used is treatment with iodide iontophoresis owing to its scavenger activity as a reducing agent and electron donor (*Adv. Clin. Path.,* 2000; 4: 11-17; *Br. J. Ophthalmol,* 2005; 89: 40-44).

Even these latter treatments, despite exerting an action which may be regarded as more relevant to treating the causes of the disease, have failed to yield the anticipated results.

The normal transparency of the cornea can be impaired by the aftermath of numerous diseases that damage the delicate structure of the various constituent components. The disease conditions most commonly implicated are post-keratitis damage, particularly after herpetic keratitis, and damage occurring in the aftermath of trauma and laser refractive surgery. The minimum common denominator is the formation of corneal opacities (leucomas) that functionally jeopardise vision. The events involved in wound healing that occur in the corneal tissue after infection, injury and refractive ablative surgery are have a profound effect on the final morphological and refractive outcomes of the restitutio ad integrum process.

The acute epithelial and stromal corneal lesions occurring immediately after injury and laser ablation are probably involved in the regulation of the subsequent corneal tissue repair events, and, among the latter, keratocyte apoptosis probably plays a major role (Cornea, 2000; 19:S7-12). This event is responsible for the corneal repair process since keratocyte apoptosis is the prime mover of the reproliferative stimulus. The stroma keratocytes underlying the initial acellular stroma therefore represent the cell source that mediates the subsequent healing of the superficial stroma beneath the epithelium. As a result of the cellular repopulation, the activated keratocytes undergo myofibroblastic transformation (*Invest. Ophthalmol. Vis, Set,* 1998; 39:487-501), thus proving responsible for the production of collagen fibres and of basic substances involved in the restituito ad integrum process. This process, however, is not self-controlled and, in many cases, abnormal, excessive healing occurs followed by a greater production of collagen and an increase in lamellar disorganisation (*Arch. Ophthalmol*, 1990; 108: 665-675). These abnormalities are involved in the pathogenesis of the most feared complication of stromal regeneration after photorefractive keratectomy (PRK), namely, haze, with consequent impairment of the functional outcome. Haze is classified according to Heitsmann in 5 degrees on the basis of the visual impairment due to the reduced corneal transparency. Though the incidence of haze has been substantially reduced over recent years, as a result of the technological advances in the field of exekner lasers, it is still a fairly frequent complication even today and, in rare cases, would appear hard to reverse, even after months of cortisone therapy. In cases of persistent haze (more than 15-18 months) which fails to respond to medical therapy (an event that can occur with late-onset haze), the only feasible procedure is phototherapeutic keratectomy (PTK) with an excimer laser, a procedure used for the laser-assisted surgical removal of superficial stromal opacities.

L-carnitine and alkanoyl L-carnitines are known compounds, whose preparation process is described in U.S. Pat. Nos. 4,439,438 and 4,254,053.

The polyunsaturated fatty acids (omega-3 fatty acids) are known for their triglyceride-lowering effects and for their effects in raising the levels of high-density lipoproteins (HDL). These fatty acids can be obtained by synthesis or, preferably, from fish oil. In that ease, it is possible to use various mixtures of omega-3 fatty acids depending oxi their characteristics. Preferably, the omega-3 fatty acids are the long-chain ones (from 20 to 22 carbon atoms). The ones most preferred are 5,8,11,14,17-eicosapentanoic acid (EPA) and cis 0,13,16,19-docosahexanoic acid (DHA). In a preferred embodiment of the invention, the omega-3 fatty acid is cis 4,7,10,13,16,19-docosahexanoic acid (DHA), most preferably in a ratio of 1:1. These omega-3 fatty acids can possibly be esterified or salified to pharmaceutically acceptable derivatives, with alcohols or bases, respectively. The omega-3 fatty acids, or their esters or salts, alone or in mixtures thereof, can be procured on the market, or can be prepared by known methods. The mixtures can be specifically formulated for the combination according to the invention.

Coenzyme Q10 is now so well known in its human use that it requires no particular explanation and the substance is available on the market. Experts in the sector can refer to the patent documents filed by the present applicant, where this substance is amply described.

Previous uses of carnitine in the ophthalmological field are already known.

U.S. Pat. No. 5,037,851 describes the use of acetyl L-carnitine for the treatment of cataract.

U.S. Pat. No. 5,145,871 and U.S. Pat. No. 5,432,199 describe the use of acetyl D-carnitine for the treatment of glaucoma.

U.S. Pat. No. 5,883,127 describes the use of acetyl L-carnitine for the treatment of maculopathy and macular degeneration.

U.S. Pat. No. 4,599,232 discloses a pharmaceutical composition containing L-carnitine or acetyl L-carnitine and coenzyme $Q_{10}$ suitable for the therapeutic treatment of atherosclerotic disorders, myocardial and coronary insufficiency and pathological conditions deriving from tissue anoxia.

Further uses of carnitine are also known.

U.S. Pat. No. 5,753,703 describes pharmaceutical composition comprising L-carnitine or an alkanoyl L-carnitine in combination with a polyunsaturated fatty acid of the omega-3 series for the prevention and the treatment of lipid metabolism disorders and cardiovascular disorders.

In Drugs Exp Clin Res 1992; 18 (8): 355-65 the use of L-carnitine in the cardiological field is described.

U.S. Pat. No. 5,543,556 describes the use of acyl L-carnitine esters with gamma-hydroxybutyric acid for the inhibition of neuronal degeneration and in the treatment of coma.

U.S. Pat. No. 5,811,457 describes tire use of propionyl L-carnitine for the treatment of chronic obliterating arteriopathy.

As above mentioned the use of Coenzyme Q10 and one omega-3 polyunsaturated fatty acid are already known.

WO00/23069 describes a compositions containing as active ingredients Coenzyme Q10 and omega-3 polyunsaturated fatty acid for the prevention and/or treatment of inherited mitochondriopathies and among the numerous pathologies cited, chronic progressive external ophthalmoplegia syndrome and retinis pigmentosa are mentioned.

None of the above-cited patents or publications describes or suggests the use of L-carnitine or of alkanoyl L-carnitine in combination with a lipid-soluble benzoquinone and a polyunsaturated fatty acids, for the preparation of a medicament for the treatment of diseases of the cornea.

In the medical field there is still a strongly perceived need for the availability of therapeutic agents useful for the treatment of the above-mentioned corneal diseases.

It has now been found that, a combination composition comprising as active ingredients:
(a) L-carnitine and/or one or more alkanoyl L-carnitines, or their pharmaceutically acceptable salts,
(b) a lipid soluble benzoquinone, and
(c) at least one omega-3 polyunsaturated fatty acid or an ester thereof; is useful for the preparation of a dietetic supplement or a medicament for the treatment of diseases of the cornea.

One object of the present invention is the use of a combination Composition comprising as active ingredients:
(a) L-carnitine and/or of one or more alkanoyl L-carnitines selected from the group consisting of acetyl, propionyl, valeryl, isovaleryl, butyryl and isobutyryl L-carnitine, or one of their pharmaceutically acceptable salts;
(b) a lipid soluble benzoquinone selected from the group consisting of Coenzyme Q10, (CoQ10) and its reduced form ubiquinol-10 (CoQ10H2), or mixtures thereof;
(c) an omega-3 polyunsaturated acid selected from the group consisting of eicosapentaenoie acid (EPA), docosahexaenoic acid (DHA) and linolenic acid (LNA), or mixtures thereof, preferred esters of LNA, EPA or DHA are the triglycerides and the ethyl ester; for preparing a dietetic supplement or a medicament for the treatment of corneal diseases in which said corneal disease is selected from the group comprising, de-epithelialising diseases, dry eye syndrome; infective keratitis; acid or alkaline caustic damages; corneal abrasions and/or injuries due to mechanical action or contact lenses; degenerative disease of the corneal stroma such as acute or chronic keratocono, stromal damages caused by refractive laser surgery; and dystrophic diseases:
  in which:
  L-carnitine (and/or an alkanoyl L-carnitine) is present preferably at a dose of 0.1-4 g, and most preferably at a dose of 0.1 g;
  omega-3 polyunsaturated fatty acid (fish oil) is present preferably at a dose of 0.1-1 g, and most preferably at a dose of 0.5 g;
  coenzyme Q10 is present preferably at a dose of 1-100 mg, and most preferably at a dose of 10 mg.

A further object of the present invention is the use of the combination composition above mentioned, for the preparation of a dietetic supplement or a medicament for the treatment of impairment of the transparency of the cornea, in which said impairment of the transparency is caused by various types of infective keratitis (viral, bacterial and fungal), or by injuries that damage the structure of the various components constituting the cornea, such as, for instance, injuries of a mechanical, post-surgical and post-laser-refractive surgery type (such as, for example, haze); hereditary or degenerative diseases such as chronic and acute keratoconus.

What is meant by pharmaceutically acceptable salt of L-carnitine is any salt of the latter with an acid that does not give rise to toxic or side effects.

These acids axe well known to pharmacologists and to experts in pharmacy. Non-limiting examples of such salts are: chloride, bromide, orotate, aspartate, acid aspartate, acid citrate, magnesium citrate, phosphate, acid phosphate, fumarate and acid fumarate, magnesium fumarate, lactate, male ate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

What is meant by pharmaceutically acceptable salt of L-carnitine is also a salt approved by the FDA and listed in the publication Int. J. of Pharm. 33 (1986), 201-217, which is incorporated herein by way of a reference.

The combination according to the invention may additionally contain other useful elements, such as antioxidants such as, for example, vitamin E and/or vitamin C; coenzyme, mineral, without this substantially impairing the activity.

The following examples illustrate the invention.

EXAMPLE 1

A clinical trial was conducted in which 40 patients suffering from dry eye syndrome were recruited.

The patients recruited were all women aged from 36 to 75 years, 30 of whom were suffering from Sjögren's syndrome, diagnosed on the basis of Fox et al.'s criteria (*Arthritis Rheum*, 1986; 29: 577-584; 1986).

Patients were selected on the basis of the BUT test, the Schirmer test, the fluorescein test and the rose bengal test (*Peseosolido* 2000; *Arch. Ophthalmol.*, 1969; 82: 10-14).

The BUT test had to yield results≦5 seconds, while the Schirmer test did not contraindicate inclusion in the trial.

Damage to the surface of the eye was evaluated by means of the rose bengal staining test and the fluorescein test. Damage in the rose Bengal staining test was determined by reference to the van Bijsterveld evaluation (*Arch. Ophthalmol.*, 1969; 82: 10-14), dividing the exposed surface into 3 zones, with a score of 0 to 3 per zone.

For abnormality of the fluorescein test score both the affected surface (A) and the damage density (D) were evaluated, with a range from 0 to 3 (low and high) on the basis of severity (*Jap. Clin. Ophthalmol;* 1994; 48: 183-188).

On the basis of the test score results, patients were divided into 3 subgroups, namely, those with mild dry eye (A1D1, A1D2, A2D1), those with moderate dry eye (A1D3, A2D2, A3D1) and those with severe dry eye (A2D3, A3D2, A3D3).

Patient were treated twice daily for 6 months with the combination composition according to the present invention having the following composition:

acetyl L-carnitine mucate 100 mg, fish oil mg 500 (containing EPA 165 mg and DHA 110 mg) and Coenzyme $Q_{10}$ 10 mg.

The results obtained are reported in the following tables.

TABLE 1/1

| Dry eye | BUT test (sec) | | P < Vs Base Line |
|---|---|---|---|
| | Base Line | End of treatment | (Wilcoxon matched pairs test) |
| Mild | 4.6 | 5.1 | <0.01 |
| Moderate | 3.8 | 4.3 | <0.01 |

TABLE 1/2

| Dry eye | Rose bengal test (score) | | P < Vs Base Line |
|---|---|---|---|
| | Base Line | End of treatment | |
| Mild | 2.4 | 2.9 | <0.05 |
| Moderate | 1.9 | 2.4 | <0.05 |
| Severe | 1.2 | 1.9 | <0.01 |

TABLE 1/3

| Dry eye | Schirmer test (mm) | | P < Vs Base Line |
|---|---|---|---|
| | Base Line | End of treatment | |
| Mild | 5.0 | 7.1 | <0.001 |
| Moderate | 3.8 | 4.8 | <0.001 |
| Severe | 2.1 | 3.7 | <0.001 |

EXAMPLE 2

In this clinical trial were enrolled 20 patients, 9 men and 11 women, ranging in age from 22 to 31 years, who had been submitted to refractive laser surgery (PRK) in both eyes with myopia not exceeding 6 diopters.

Patients were divided in two groups 10 patients each (control and treated group respectively).

Patients were treated twice daily with the combination composition according to the invention described in Example 1.

The eyes of both groups (treated and control) were also treated with antibiotic eye-drops for 4 days, and a hydrogel contact lens was applied to both eyes after PRK for the first 5 days postoperatively.

The efficacy of adequate re-epithelialisation after PRK was evaluated before the treatment and after 7 days, 1 and 6 months of treatment.

Since the vision of an object or image cannot be limited to minimum separable perception (visual acuity), one important parameter evaluated was the contrast of the object. To study this parameter, the perception threshold was measured for a whole range of objects of various sizes with increasingly reduced contrasts. The resulting assessment was the spatial contrast sensitivity function (spatial CSF) (*Pescosolido* 2001). For this function, test images were mainly used consisting of stripes with a sinusoidal luminance profile. These bars, alternating dark and Light, were defined by their spatial frequency [cycles per degree (CPD) or number of pairs of stripes (black/white) per degree of visual angle] and by their contrast. The inverse of contrast (C) was contrast sensitivity (S) (S=1/C). Contrast is often expressed in terms of percentages, 98% being very high, and 3% very low (*Pescosolido* 2001).

The contrast sensitivity test was performed using the Optec 6500 vision tester capable of receiving ETDRS and FACT test scores and software for the management and analysis of contrast sensitivity data. The system was capable of simulating the way in which the patient actually saw things. Moreover, it was capable of comparing patient simulations with standard representations. The examination was performed first after 7 days and then at 3 and 6 months postoperatively. Patients started treatment immediately after PRK.

The results obtained are reported in Table 2.

TABLE 2

| | CONTRAST SENSITIVITY (%) | | |
|---|---|---|---|
| | Treated group | control | P < Vs Control |
| Base Line | 78 | 77 | ns |
| 7 day | 52 | 48 | <0.05 |
| 1 month | 62 | 56 | <0.01 |
| 6 months | 74 | 64 | <0.01 |

EXAMPLE 3

In this clinical trial were recruited 14 patients, who had been submitted to refractive laser surgery (PRK) in both eyes with myopia not exceeding 10 diopters (3-10 diopters).

Patients were divided in two groups (7 patients each).

Group 1 (7 patients) received postoperative standard treatment consisting of eye drops containing corticosteroids and antibiotics and ocular drops (artificial tears) containing hyaluronic acid.

Group 2 (7 patients) received the same treatment of group 1 and the composition according to the present invention described in Example 1, twice daily.

The treatment started 30 day before the refractive laser surgery and was continued for 6 months after the surgery.

The following parameters were controlled at the beginning, and after 1 and 6 months of treatment.

(1) irritation symptoms (by a questionnaire):
Irritation symptoms were subdivided in 3 groups:
(i) dysestesia: foreign body sensation, dryness, burning, difficulty blinking;
(ii) hyperestesia: particular sensitivity to: the air flow (wind, air conditioned, powder, smog, smoke); topical medications; eye fatigue and pain; frequent blinking; higher tear production; and photophobia;
(iii) daily variation of the symptoms.
(2) inflammatory sign by slit-lamp examination:
Two subgroup of inflammatory signs were also recorded:
(i) hyperemia and papillary hypertrophy of the conjunctiva,
(ii) discharge (particulate matter in the tear film, plugged Meibomian glands, blurred vision improving with blinking due to mucus on the ocular surface, mucus thread at the inner canthus or in the lower fornix, difficulties of opening the eye upon waking).
(3) tear flow by modified Schirmer test (Cornea. 2003 May; 22 (4):285-7) and BUT test.
(4) daily frequency of treatment with artificial tear.
(5) corneal sensitivity with Cochet-Bonnet estesiometer (Can J Ophthalmol. 2004; December; 39 (7):767-71).

For evaluation of irritation symptoms and inflammatory signs the following score system was applied:
score 0=no;
score 1=mild;
score 2=medium;
score 3=severe.
The mean score of both eyes were considered.

The results obtained are reported in the following tables.

TABLE 3/1

| | Symptoms of irritation | | |
|---|---|---|---|
| | Treated group | Control group | P < Vs Control |
| Base Line | 0.9 | 0.9 | ns |
| 1 month | 1.8 | 2.3 | <0.01 |
| 6 months | 1.2 | 1.7 | <0.001 |

Postoperative irritation symptoms decreased more rapidly in the treated group as compared to the control. The difference was significant after 1 month ($p<0.01$) and after 6 months ($p<0.01$).

TABLE 3/2

| | Signs of inflammation. | | |
|---|---|---|---|
| | Treated group | Control group | P < Vs Control |
| basal | 0.5 | 0.5 | ns |
| 1 month | 1.1 | 1.9 | <0.01 |
| 6 months | 0.6 | 1.0 | <0.01 |

Postoperative inflammatory signs decreased more rapidly in the treated group as compared to the control. The difference was significant after 1 month ($p<0.01$) and 6 months ($p<0.01$).

TABLE 3/3

| | Frequency of topical treatment | | |
|---|---|---|---|
| | Treated group | Control group | P < Vs Control |
| basal | 0.3 | 0.4 | Ns |
| 1 month | 3.2 | 3.8 | <0.05 |
| 6 months | 1.1 | 3.2 | <0.001 |

In the postoperative period the mean number of daily installation of tear substitutes was significantly lower in the treated group compared to controls ($p<0.05$ and $p<0.001$)

TABLE 3/4

| | Corneal sensitivity | | |
|---|---|---|---|
| | Treated group | Control group | P < Vs Control |
| basal | 100 | 100 | ns |
| 1 month | 54 | 48 | <0.01 |
| 6 months | 76 | 58 | <0.001 |

Corneal sensitivity dramatically decreased after laser surgery. However, the recovery was significantly enhanced in treated group compared to controls ($p<0.01$ and 0.001).

The results obtained, above reported, show that the combination composition according to the present invention improves the regeneration of sensory nerves of the cornea after laser refractive surgery and subsequently improve postoperative dry eye symptoms.

The acetyl L-carnitine, omega-3 fatty acids and coenzyme $Q_{10}$ can be in any form suitable for oral administration in human subjects.

On the basis of various factors such as the concentration of active ingredient and the subject condition, the composition according to the invention can be marketed as a health food supplement, nutritional supplement, or as a therapeutic product.

The nutritional supplement according to the present invention can be prepared by mixing the active ingredient (acetyl L-carnitine, omega-3 fatty acids and coenzyme $Q_{10}$) with excipients suitable for the formulation of compositions for oral administration.

Said excipients are well known to experts in pharmaceutical, technology.

In the following is reported a non limiting example of a composition according to the present invention:

Acetyl L-carnitine mucate 100 mg;
Fish oil 500 mg (containing EPA 165 mg and DHA 110 mg);
Coenzyme $Q_{10}$ 10 mg.

The invention claimed is:

1. A method of treating corneal diseases, comprising administering to a patient in need thereof an effective amount of a combination composition comprising as active ingredients:
   (a) 0.1 to 4 g of L-carnitine and/or one or more alkanoyl L-carnitine, or one of their pharmaceutically acceptable salts, wherein said alkanoyl L-carnitine is selected from the group consisting of acetyl, propionyl, valeryl, isovaleryl, butyryl, and isobutyryl L-carnitine, or one of their pharmaceutically acceptable salts;
   (b) 0.1 to 1 g of a lipid soluble benzoquinone; and
   (c) 1 to 10 mg of an omega-3 polyunsaturated fatty acid: and treating said corneal disease in said patient.

2. Method according to claim 1, wherein the corneal disease is an impairment of the corneal transparency.

3. Method according to claim 1, in which the pharmaceutically acceptable salts of L-carnitine or alkanoyl L-carnitine is selected from the group consisting of: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

4. Method according to claim 1, in which the lipid soluble benzoquinone is selected from the group consisting of Coenzyme Q10 (CoQ10) and ubiquinol-10 (CoQ10H2); and mixtures thereof.

5. Method according to claim 1, in which the omega-3 polyunsaturated fatty acid is selected from the group consisting of eicosapentaenoic acid (EPA), docosahexaenoic acid (DHA) and linolenic acid (LNA) and mixtures thereof.

6. Method according to claim 1, in which the corneal disease is selected from the group consisting of, de-epithelialising diseases, dry eye syndrome; infective keratitis; acid or alkaline caustic damages; corneal abrasions and/or injuries; hereditary or degenerative disease; and dystrophic diseases.

7. Method according to claim 6, wherein the infective keratitis is due to viral, bacterial or fungal infection.

8. Method according to claim 6, wherein the abrasions and/or injuries are due to mechanical action, contact lenses, post-surgical or post-laser-refractive therapy.

9. Method according to claim 6, wherein the hereditary or degenerative disease is acute or chronic keratocono.

10. Method according to claim 8, wherein the post-surgical or post-laser-refractive surgery damages is haze.

11. Method according to claim 1, wherein combination composition comprises: Acetyl L-carnitine mucate 100 mg; Fish oil 500 mg; Coenzyme $Q_{10}$ 10 mg.

12. Method according to claim 11, wherein the Fish oil contains 165 mg of EPA and 110 mg of DHA.

13. Method according to claim 1, wherein said effective amount corresponds to 0.1 g of L-carnitine or an alkanoyl L-carnitine, 0.5 g of omega-3 polyunsaturated fatty acid and 10 mg of coenzyme Q 10.

* * * * *